(12) United States Patent
Mouser

(10) Patent No.: US 9,775,346 B1
(45) Date of Patent: Oct. 3, 2017

(54) HAND SANITIZER COMPOSITION AND METHOD OF MANUFACTURE

(71) Applicant: Glenn Mouser, Boise, ID (US)

(72) Inventor: Glenn Mouser, Boise, ID (US)

(73) Assignee: Roger Wilson, Boise, ID (US)

( * ) Notice: Subject to any disclaimer, the term of this patent is extended or adjusted under 35 U.S.C. 154(b) by 0 days.

(21) Appl. No.: 15/088,553

(22) Filed: Apr. 1, 2016

(51) Int. Cl.
| A01N 33/12 | (2006.01) |
| A01N 25/02 | (2006.01) |
| A61K 8/34 | (2006.01) |
| A61K 8/41 | (2006.01) |
| A61Q 19/00 | (2006.01) |

(52) U.S. Cl.
CPC ............ *A01N 33/12* (2013.01); *A01N 25/02* (2013.01); *A61K 8/342* (2013.01); *A61K 8/416* (2013.01); *A61Q 19/007* (2013.01); *A61K 2800/596* (2013.01); *A61K 2800/74* (2013.01)

(58) Field of Classification Search
None
See application file for complete search history.

(56) References Cited

U.S. PATENT DOCUMENTS

| 6,087,400 A | 7/2000 | Dyer et al. |
| 6,846,846 B2 | 1/2005 | Modak et al. |
| 8,802,607 B2 | 8/2014 | Fan et al. |
| 8,865,195 B2 | 10/2014 | Wolff et al. |
| 2007/0241306 A1 | 10/2007 | Wehner et al. |
| 2008/0213192 A1 | 9/2008 | Schlesinger et al. |
| 2009/0175808 A1* | 7/2009 | Galley .................... A61K 8/06 514/1.1 |
| 2009/0226498 A1 | 9/2009 | Flugge-Berendes et al. |
| 2010/0316747 A1 | 12/2010 | Ge et al. |
| 2011/0207832 A1 | 8/2011 | Roszell et al. |
| 2011/0262558 A1 | 10/2011 | Huckfeldt et al. |
| 2012/0034314 A1 | 2/2012 | Levison et al. |
| 2013/0287712 A1 | 10/2013 | Wolff et al. |
| 2014/0017184 A1 | 1/2014 | Fumagalli et al. |
| 2014/0171513 A1 | 6/2014 | Seidling et al. |
| 2014/0315995 A1* | 10/2014 | Dreher .................. A61K 31/375 514/458 |
| 2014/0364509 A1 | 12/2014 | Wegner et al. |
| 2015/0272124 A1 | 10/2015 | Pedersen et al. |

* cited by examiner

*Primary Examiner* — Ernest V Arnold
*Assistant Examiner* — Kyung Sook Chang
(74) *Attorney, Agent, or Firm* — Jason P. Webb; Pearson Butler

(57) ABSTRACT

A hand sanitizing composition and a method of manufacture, wherein the composition includes a solvent from about 78% to about 96% by weight sufficient to operate as a carrier and solvent. The composition includes tetrasodium EDTA and/or Sodium Citrate from about 0.01% to about 1% by weight to operate as a buffer, stabilizer and chelating agent. The composition includes a humectant selected from the group of humectants consisting of: Cetyl Alcohol, Ceteryl Alcohol, and Steryl Alcohol from about 1.5% to about 5.5% by weight to emulsify, thicken and lubricate. The composition includes an emollient from about 0.1% to about 3.2% by weight and an antioxidant vitamin from about 0.01% to about 1% by weight. The composition includes a soothing agent in a therapeutically significant amount and a conditioner.

18 Claims, 1 Drawing Sheet

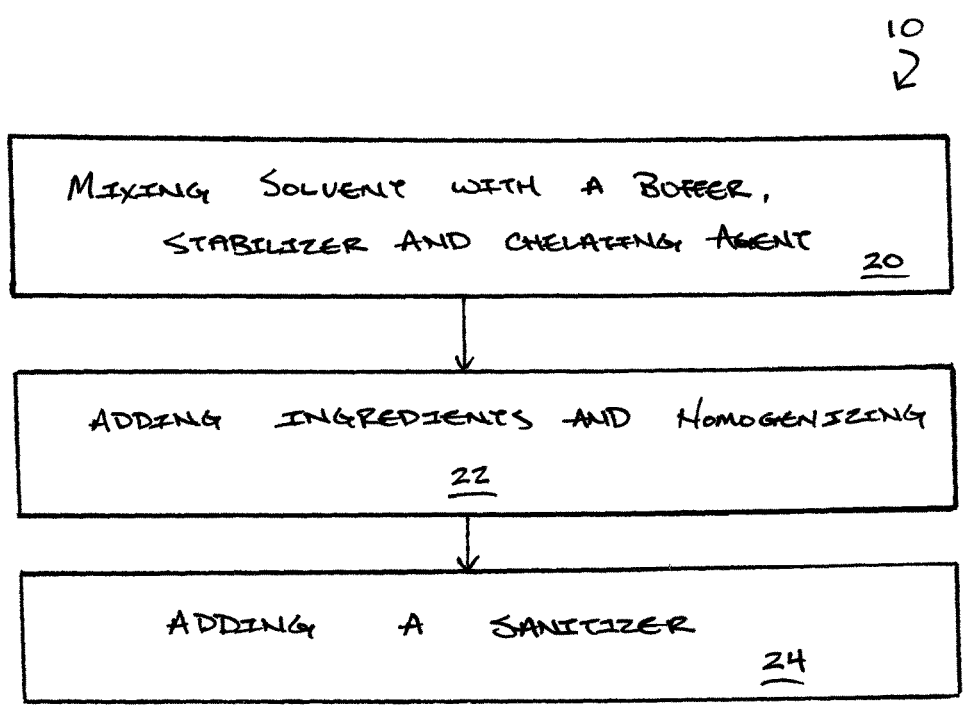

HAND SANITIZER COMPOSITION AND METHOD OF MANUFACTURE

CROSS-REFERENCE TO RELATED APPLICATIONS

This invention claims priority, under 35 U.S.C. §120, to the U.S. Provisional Patent Application No. 62/141,533 to Glen Mouser filed on Apr. 1, 2015, which is incorporated by reference herein.

BACKGROUND OF THE INVENTION

Field of the Invention

The present invention relates to sanitizers, specifically a hand sanitizer composition and method of manufacture.

Description of the Related Art

A hand antiseptic, hand disinfectant, or hand sanitizer is a supplement or alternative to hand washing with soap and water. Many preparations are available, including gel, foam, and liquid solutions. The active ingredient in hand sanitizers may be isopropyl alcohol (isopropanol), ethanol, n-propanol, or povidone-iodine. Inactive ingredients in alcohol rubs typically include a thickening agent such as polyacrylic acid for alcohol gels, humectants such as glycerin for liquid rubs, propylene glycol, and essential oils of plants. Alcohol-based hand sanitizers are more effective at killing microorganisms than soaps and do not dry out hands as much.

Common non-alcohol, rinse-free hand sanitizers use either small concentrations of the nitrogenous cationic surface-acting agent benzalkonium chloride, the chlorinated aromatic compound triclosan, or povidone-iodine. Some products claim to kill microorganisms naturally, although these claims are not substantiated in any FDA monograph. All hand sanitizer products require National Drug Code designation in the United States and natural product number designation in Canada.

Some improvements have been made in the field. Examples of references related to the present invention are described below in their own words, and the supporting teachings of each reference are incorporated by reference herein:

U.S. Pat. No. 8,865,195, issued to Wolff et al., discloses foaming formulations including silicone polyesters are disclosed. These foaming formulations are useful as cleansing formulations such as used in liquid hand cleansers and wet wipes. The foaming formulations provide improved aesthetic properties and foaming appearance, while maintaining high antimicrobial capacity.

U.S. Pat. No. 6,846,846, issued to Modak et al., discloses antimicrobial compositions having synergistic combinations of octoxyglycerin and at least one other antimicrobial agent in formulations which are more effective than prior art compositions without causing increased irritation to the skin of the average user. In certain embodiments, skin irritation may be minimized by low concentrations of antimicrobials and/or the presence of soothing compounds such as zinc. Preferred embodiments include combinations of octoxyglycerin, a quaternary compound, and at least one other antimicrobial agent. Without being bound to any particular theory, it is hypothesized that the unexpected antimicrobial effectiveness of combinations of octoxyglycerin may result from an enhancement of the permeability of microbes to antimicrobials caused by octoxyglycerin.

U.S. Pat. No. 6,087,400, issued to Dyer et al., discloses antimicrobial compositions and methods for preparing and using same are provided. The antimicrobial compositions are surfactant-based and contain certain benzalkonium chloride homologs. The compositions are useful in treating infections in animals and humans, and can be applied to areas including the skin, nails, and mouth.

U.S. Patent Application Publication No.: 2015/0272124, by Pedersen et al., discloses an antimicrobial composition of the present invention comprises a cationic active ingredient, a foam boosting surfactant, a foam boosting copolymer, a foam stabilizer, and a chelating agent. The present antimicrobial compositions are free of the antimicrobial agent triclosan (i.e., 2,4,4'-trichloro-2'hydroxy-diphenylether), have rapid cidal activity, provide stable copious foam and exhibit enhanced tissue (e.g. skin) compatibility as defined by an in vitro whole toxicology assessment method.

U.S. Patent Application Publication No.: 2011/0262558, by Huckfeldt et al., discloses an improved composition for skin cleansing and protection is disclosed. The composition contains an effective amount of at least one alpha-hydroxyl acid or a pharmaceutically acceptable salt thereof, at least one base, one surfactant and one skin protectant. Various additives and excipients may be included in the formulation. The improved composition disclosed herein achieves a higher bacteria killing rate and shows longer action duration. The disclosed composition is capable of penetrating deep into the skin which allows for delivery of more antimicrobials to sites that are at a higher risk of being infected. Various modifications of the improved composition are also disclosed.

U.S. Patent Application Publication No.: 2009/0226498, by Flugge-Berendes et al., discloses moisturizing hand sanitizers including alcohols that are effective in killing microorganisms while providing a moisturizing benefit to the user's skin. More particularly, the alcohol-based hand sanitizers include a high internal phase emulsion which allows moisturizers or skin protectants such as emollients and/or silicones to be stably incorporated into the sanitizer.

The inventions heretofore known suffer from a number of disadvantages which include being limited in composition, being limited in use, being limited in ingredients, being limited in effectiveness, being limited in efficiency, being expensive, being limited in application, and the like.

What is needed is a hand sanitizer, sanitizing composition, and/or method of manufacture of the same that solves one or more of the problems described herein and/or one or more problems that may come to the attention of one skilled in the art upon becoming familiar with this specification.

SUMMARY OF THE INVENTION

The present invention has been developed in response to the present state of the art, and in particular, in response to the problems and needs in the art that have not yet been fully solved by currently available hand sanitizers. Accordingly, the present invention has been developed to provide an effective and efficient hand sanitizer.

According to one embodiment of the invention, there is a hand sanitizing composition that may include a solvent from about 78% to about 96% by weight sufficient to operate as a carrier and solvent for the composition. The composition may include tetrasodium EDTA and/or Sodium Citrate from about 0.01% to about 1% by weight to operate as a buffer, stabilizer and chelating agent. The composition may include a humectant selected from the group of humectants consisting of: Cetyl Alcohol, Ceteryl Alcohol, and Steryl Alcohol from about 1.5% to about 5.5% by weight to emulsify, thicken and lubricate.

The hand sanitizing composition may include an emollient from about 0.1% to about 3.2% by weight. The composition may include an antioxidant vitamin from about 0.01% to about 1% by weight. The composition may include a soothing agent in a therapeutically significant amount. The hand sanitizing composition may include a conditioner selected from the group of conditioners consisting of: Stearylkonium Chloride, Behentrimonium Chloride and Cetrimonium Chloride from an amount of about 0.1% to about 3.1% by weight.

The hand sanitizing composition may include a non-ionic surfactant from about 0.02% to about 7.9% by weight. The composition may include a preservative from about 0.1% to about 1.8% by weight. The composition may include a sanitizer selected from the group of sanitizers consisting of: Benzalkonium Chloride and Benzathonium Chloride from an amount of about 0.01% to about 0.13% by weight sufficient to sanitize hands during the use of the composition. The composition may include a biostatic antimicrobial.

According to one embodiment of the invention, there is a hand sanitizing composition that may consist essential of a solvent from about 78% to about 96% by weight sufficient to operate as a carrier and solvent for the composition. The composition may include tetrasodium EDTA and/or Sodium Citrate from about 0.01% to about 1% by weight to operate as a buffer, stabilizer and chelating agent. The composition may include a humectant selected from the group of humectants consisting of: Cetyl Alcohol, Ceteryl Alcohol, and Steryl Alcohol from about 1.5% to about 5.5% by weight to emulsify, thicken and lubricate.

The hand sanitizing composition may include an emollient from about 0.1% to about 3.2% by weight. The composition may include an antioxidant vitamin from about 0.01% to about 1% by weight. The composition may include a soothing agent in a therapeutically significant amount. The composition may include a conditioner selected from the group of conditioners consisting of: Stearylkonium Chloride, Behentrimonium Chloride and Cetrimonium Chloride from an amount of about 0.1% to about 3.1% by weight.

The hand sanitizing composition may include a non-ionic surfactant from about 0.02% to about 7.9% by weight. The composition may include a preservative from about 0.1% to about 1.8% by weight. The composition may include a sanitizer selected from the group of sanitizers consisting of: Benzalkonium Chloride and Benzathonium Chloride from an amount of about 0.01% to about 0.13% by weight sufficient to sanitize hands during the use of the composition.

According to one embodiment of the invention, there is a method of manufacturing a hand sanitizer that may include the steps of mixing together in a vessel, using heat as needed a solvent from about 78% to about 96% by weight sufficient to operate as a carrier and solvent for the composition; and tetrasodium EDTA and/or Sodium Citrate from about 0.01% to about 1% by weight to operate as a buffer, stabilizer and chelating agent.

The method of manufacturing a hand sanitizer may include the step of adding the following ingredients and homogenizing a humectant selected from the group of humectants consisting of: Cetyl Alcohol, Ceteryl Alcohol, and Steryl Alcohol from about 1.5% to about 5.5% by weight to emulsify, thicken and lubricate; an emollient from about 0.1% to about 3.2% by weight; an antioxidant vitamin from about 0.01% to about 1% by weight; a soothing agent in a therapeutically significant amount; a conditioner selected from the group of conditioners consisting of: Stearylkonium Chloride, Behentrimonium Chloride and Cetrimonium Chloride from an amount of about 0.1% to about 3.1% by weight; a non-ionic surfactant from about 0.02% to about 7.9% by weight; and a preservative from about 0.1% to about 1.8% by weight.

The method of manufacturing a hand sanitizer may include the step of adding, sufficiently slowly while mixing to prevent undesired effects, a sanitizer selected from the group of sanitizers consisting of: Benzalkonium Chloride and Benzathonium Chloride from an amount of about 0.01% to about 0.13% by weight sufficient to sanitize hands during the use of the composition.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

These features and advantages of the present invention will become more fully apparent from the following description and appended claims, or may be learned by the practice of the invention as set forth hereinafter.

BRIEF DESCRIPTION OF THE DRAWINGS

In order for the advantages of the invention to be readily understood, a more particular description of the invention briefly described above will be rendered by reference to specific embodiments that are illustrated in the appended drawing(s). It is noted that the drawings of the invention are not to scale. The drawings are mere schematics representations, not intended to portray specific parameters of the invention. Understanding that these drawing(s) depict only typical embodiments of the invention and are not, therefore, to be considered to be limiting its scope, the invention will be described and explained with additional specificity and detail through the use of the accompanying drawing(s), in which:

FIG. 1 is a flowchart of a method of manufacturing a hand sanitizer, according to one embodiment of the invention.

DETAILED DESCRIPTION OF THE INVENTION

For the purposes of promoting an understanding of the principles of the invention, reference will now be made to the exemplary embodiments illustrated in the drawing(s), and specific language will be used to describe the same. It will nevertheless be understood that no limitation of the scope of the invention is thereby intended. Any alterations and further modifications of the inventive features illustrated herein, and any additional applications of the principles of the invention as illustrated herein, which would occur to one skilled in the relevant art and having possession of this disclosure, are to be considered within the scope of the invention.

Reference throughout this specification to an "embodiment," an "example" or similar language means that a particular feature, structure, characteristic, or combinations thereof described in connection with the embodiment is included in at least one embodiment of the present invention. Thus, appearances of the phrases an "embodiment," an "example," and similar language throughout this specification may, but do not necessarily, all refer to the same embodiment, to different embodiments, or to one or more of the figures. Additionally, reference to the wording "embodiment," "example" or the like, for two or more features, elements, etc. does not mean that the features are necessarily related, dissimilar, the same, etc.

Each statement of an embodiment, or example, is to be considered independent of any other statement of an embodiment despite any use of similar or identical language characterizing each embodiment. Therefore, where one embodiment is identified as "another embodiment," the identified embodiment is independent of any other embodiments characterized by the language "another embodiment." The features, functions, and the like described herein are considered to be able to be combined in whole or in part one with another as the claims and/or art may direct, either directly or indirectly, implicitly or explicitly.

As used herein, "comprising," "including," "containing," "is," "are," "characterized by," and grammatical equivalents thereof are inclusive or open-ended terms that do not exclude additional unrecited elements or method steps. "Comprising" is to be interpreted as including the more restrictive terms "consisting of" and "consisting essentially of."

FIG. 1 is a flowchart of a method of manufacturing a hand sanitizer, according to one embodiment of the invention. There is shown a method of manufacturing a hand sanitizer 10 including the following steps.

The illustrated method of manufacturing a hand sanitizer 10 includes the step of mixing together in a vessel, using heat as needed, a solvent from about 78% to about 96% by weight sufficient to operate as a carrier and solvent for the composition and adding tetrasodium EDTA and/or Sodium Citrate from about 0.01% to about 1% by weight to operate as a buffer, stabilizer and chelating agent to the solvent 20.

The method of manufacturing a hand sanitizer 10 includes the step of adding the following ingredients and homogenizing a humectant selected from the group of humectants consisting of: Cetyl Alcohol, Ceteryl Alcohol, and Steryl Alcohol from about 1.5% to about 5.5% by weight to emulsify, thicken and lubricate; an emollient from about 0.1% to about 3.2% by weight; an antioxidant vitamin from about 0.01% to about 1% by weight; a soothing agent in a therapeutically significant amount; a conditioner selected from the group of conditioners consisting of: Stearylkonium Chloride, Behentrimonium Chloride and Cetrimonium Chloride from an amount of about 0.1% to about 3.1% by weight; a non-ionic surfactant from about 0.02% to about 7.9% by weight; and a preservative from about 0.1% to about 1.8% by weight 22.

The method of manufacturing a hand sanitizer may include the step of adding, sufficiently slowly while mixing to prevent undesired effects, a sanitizer selected from the group of sanitizers consisting of: Benzalkonium Chloride and Benzathonium Chloride from an amount of about 0.01% to about 0.13% by weight sufficient to sanitize hands during the use of the composition 24.

According to one embodiment of the invention, there is a hand sanitizing composition that includes a solvent from about 78% to about 96% by weight sufficient to operate as a carrier and solvent for the composition. The composition includes tetrasodium EDTA and/or Sodium Citrate from about 0.01% to about 1% by weight to operate as a buffer, stabilizer and chelating agent. The composition includes a humectant selected from the group of humectants consisting of: Cetyl Alcohol, Ceteryl Alcohol, and Steryl Alcohol from about 1.5% to about 5.5% by weight to emulsify, thicken and lubricate.

The hand sanitizing composition includes an emollient from about 0.1% to about 3.2% by weight. The composition includes an antioxidant vitamin from about 0.01% to about 1% by weight. The composition includes a soothing agent in a therapeutically significant amount. The hand sanitizing composition includes a conditioner selected from the group of conditioners consisting of: Stearylkonium Chloride, Behentrimonium Chloride and Cetrimonium Chloride from an amount of about 0.1% to about 3.1% by weight.

The hand sanitizing composition includes a non-ionic surfactant from about 0.02% to about 7.9% by weight. The composition includes a preservative from about 0.1% to about 1.8% by weight. The composition includes a sanitizer selected from the group of sanitizers consisting of: Benzalkonium Chloride and Benzathonium Chloride from an amount of about 0.01% to about 0.13% by weight sufficient to sanitize hands during the use of the composition. The composition includes a biostatic antimicrobial. The biostatic antimicrobial may be such as that produced under the brand name BioProtect (aka antimicrobial silicon quat) by Chemex Industries, Inc. of Irvine Calif.

According to one embodiment of the invention, there is a hand sanitizing composition that is consisting essential of a solvent from about 78% to about 96% by weight sufficient to operate as a carrier and solvent for the composition. The composition includes tetrasodium EDTA and/or Sodium Citrate from about 0.01% to about 1% by weight to operate as a buffer, stabilizer and chelating agent. The composition includes a humectant selected from the group of humectants consisting of: Cetyl Alcohol, Ceteryl Alcohol, and Steryl Alcohol from about 1.5% to about 5.5% by weight to emulsify, thicken and lubricate.

The hand sanitizing composition includes an emollient from about 0.1% to about 3.2% by weight. The composition includes an antioxidant vitamin from about 0.01% to about 1% by weight. The composition includes a soothing agent in a therapeutically significant amount. The composition includes a conditioner selected from the group of conditioners consisting of: Stearylkonium Chloride, Behentrimonium Chloride and Cetrimonium Chloride from an amount of about 0.1% to about 3.1% by weight.

The hand sanitizing composition includes a non-ionic surfactant from about 0.02% to about 7.9% by weight. The composition includes a preservative from about 0.1% to about 1.8% by weight. The composition includes a sanitizer selected from the group of sanitizers consisting of: Benzalkonium Chloride and Benzathonium Chloride from an amount of about 0.01% to about 0.13% by weight sufficient to sanitize hands during the use of the composition.

According to one embodiment of the invention, there is a hand sanitizer lotion that may be of medical grade and/or may be for personal use and/or for use by medical personnel. A formula may, when combined as explained, offer a high degree of bactericidal efficacy. The formula may be a cold or hot mix formula based upon ingredients chosen as some ingredients will mix better when heat is applied before, during and/or after the mixing thereof.

The formula includes one or more of: Water from about 78 to about 96% by weight to operate as an excipient, carrier and/or a solvent; Tetrasodium EDTA (a chelating agent) and/or Sodium Citrate from about 0.01 to about 1% by weight to operate as a buffer, water stabilizer, pH stabilizer, chelating agent and/or to otherwise influence the mixing, emulsification, acidity regulation, and/or the like thereof of the mixture; Cetyl Alcohol and/or Ceteryl Alcohol and/or Steryl Alcohol from about 1.5% to about 5.5% by weight to emulsify, serve as a humectant, thicken, and/or lubricate; Dimethicone (silicone) and/or an ester similar Octyl Palmitate and/or Isopropyl Myristate and/or Sorbitan Laurate from about 0.1 to about 3.2% to serve as an emollient, glide, protectant and/or body builder; Vitamin E Tocopherol and/or Vitamin A Palmitate from about 0.01 to about 1% by weight to serve as an antioxidant, emollient and/or a humectant; Hyaluronic Acid or Glycerin and/or Aloe Vera and/or similar humectant from about 0.001 to about 1.2% by weight to serve as a soothing agent, humectant, and/or thickener; Stearylkonium Chloride and/or Behentrimonium Chloride and/or Cetrimonium chloride from about 0.1 to about 3.1% by weight to serve as a conditioner and/or a stabilizer; a surfactant that is cationic and/or non-ionic such but not limited to a polysorbate 20, 60, 80 and/or cocamidopropyl betaine from about 0.02 to about 7.9% by weight to serve as a cleaner, detergent, surfactant, and/or emulsifier; a Preservative System (phenoxyethanol, caprylyl glycol, sorbic acid) and/or preservative similar and/or compatable with one or more ingredients from about 0.1 to about 1.8% by weight as a broad spectrum preservative; and/or Benzalkonium Chloride and/or Benzathonium Chloride from about 0.01 to about 0.13% by weight to serve as an Active Ingredient for the purpose of sanitizing hands.

To mix, perform one or more of the following steps: in an adequate vessel, put water and EDTA and mix; heat as necessary to melt or dissolve ingredients chosen; add balance of ingredients and high speed mix or homogenize until smooth; add the Active Ingredient very, very slowly and continue mixing until smooth; and/or pour off and fill containers.

It is understood that the above-described embodiments are only illustrative of the application of the principles of the present invention. The present invention may be embodied in other specific forms without departing from its spirit or essential characteristics. The described embodiment is to be considered in all respects only as illustrative and not restrictive. The scope of the invention is, therefore, indicated by the appended claims rather than by the foregoing description. All changes which come within the meaning and range of equivalency of the claims are to be embraced within their scope.

Thus, while the present invention has been fully described above with particularity and detail in connection with what is presently deemed to be the most practical and preferred embodiment of the invention, it will be apparent to those of ordinary skill in the art that numerous modifications, including, but not limited to, variations in size, materials, shape, form, function and manner of operation, assembly and use may be made, without departing from the principles and concepts of the invention as set forth in the claims. Further, it is contemplated that an embodiment may be limited to consist of or to consist essentially of one or more of the features, functions, structures, methods described herein.

What is claimed is:
1. A hand sanitizing composition, comprising:
   a. water from about 78% to about 96% by weight sufficient to operate as a carrier and solvent for the composition;
   b. tetrasodium EDTA and/or Sodium Citrate from about 0.01% to about 1% by weight to operate as a buffer, stabilizer and chelating agent;
   c. a humectant selected from the group of humectants consisting of: Cetyl Alcohol, Ceteryl Alcohol, and Steryl Alcohol from about 1.5% to about 5.5% by weight to emulsify, thicken and lubricate;
   d. an emollient from about 0.1% to about 3.2% by weight;
   e. an antioxidant vitamin from about 0.01% to about 1% by weight;
   f. a soothing agent;
   g. a conditioner selected from the group of conditioners consisting of: Stearylkonium Chloride, Behentrimonium Chloride and Cetrimonium Chloride from an amount of about 0.1% to about 3.1% by weight;
   h. a non-ionic surfactant from about 0.02% to about 7.9% by weight;
   i. a preservative from about 0.1% to about 1.8% by weight; and
   j. a sanitizer selected from the group of sanitizers consisting of: Benzalkonium Chloride and Benzathonium Chloride from an amount of about 0.01% to about 0.13% by weight sufficient to sanitize hands during the use of the composition.

2. The composition of claim 1, further comprising a biostatic antimicrobial.

3. A hand sanitizing composition, consisting of:
   a. a solvent from about 78% to about 96% by weight sufficient to operate as a carrier and solvent for the composition;
   b. tetrasodium EDTA and/or Sodium Citrate from about 0.01% to about 1% by weight to operate as a buffer, stabilizer and chelating agent;
   c. a humectant selected from the group of humectants consisting of: Cetyl Alcohol, Ceteryl Alcohol, and Steryl Alcohol from about 1.5% to about 5.5% by weight to emulsify, thicken and lubricate;
   d. an emollient from about 0.1% to about 3.2% by weight;
   e. an antioxidant vitamin from about 0.01% to about 1% by weight;
   f. a soothing agent;
   g. a conditioner selected from the group of conditioners consisting of: Stearylkonium Chloride, Behentrimonium Chloride and Cetrimonium Chloride from an amount of about 0.1% to about 3.1% by weight;
   h. a non-ionic surfactant from about 0.02% to about 7.9% by weight;
   i. a preservative from about 0.1% to about 1.8% by weight; and
   j. a sanitizer selected from the group of sanitizers consisting of: Benzalkonium Chloride and Benzathonium Chloride from an amount of about 0.01% to about 0.13% by weight sufficient to sanitize hands during the use of the composition.

4. A method of manufacturing a hand sanitizer, comprising the steps of:
   a. mixing together in a vessel, using heat as needed:
      i. a solvent from about 78% to about 96% by weight sufficient to operate as a carrier and solvent for the composition; and
      ii. tetrasodium EDTA and/or Sodium Citrate from about 0.01% to about 1% by weight to operate as a buffer, stabilizer and chelating agent;

b. then adding the following ingredients and homogenizing:
  iii. a humectant selected from the group of humectants consisting of: Cetyl Alcohol, Ceteryl Alcohol, and Steryl Alcohol from about 1.5% to about 5.5% by weight to emulsify, thicken and lubricate;
  iv. an emollient from about 0.1% to about 3.2% by weight;
  v. an antioxidant vitamin from about 0.01% to about 1% by weight;
  vi. a soothing agent;
  vii. a conditioner selected from the group of conditioners consisting of: Stearylkonium Chloride, Behentrimonium Chloride and Cetrimonium Chloride from an amount of about 0.1% to about 3.1% by weight;
  viii. a non-ionic surfactant from about 0.02% to about 7.9% by weight; and
  ix. a preservative from about 0.1% to about 1.8% by weight; and
c. then adding, sufficiently slowly while mixing to prevent undesired effects, a sanitizer selected from the group of sanitizers consisting of: Benzalkonium Chloride and Benzathonium Chloride from an amount of about 0.01% to about 0.13% by weight sufficient to sanitize hands during the use of the composition.

5. The composition of claim 1, wherein the alcohol content of the composition is limited to no greater than 5.5% by weight.

6. The composition of claim 2, wherein the alcohol content of the composition is limited to no greater than 5.5% by weight.

7. The composition of claim 1, wherein the antioxidant comprises an antioxidant selected from the group of antioxidants consisting of Vitamin E Tocopherol and Vitamin A Palmitate.

8. The composition of claim 7, further comprising a biostatic antimicrobial.

9. The composition of claim 1, wherein the emollient comprises an emollient selected from the group of emollients consisting of: Dimethicone, Octyl Palmitate, Isopropyl Myristate, and Sorbitan Laurate.

10. The composition of claim 3, wherein the alcohol content of the composition is limited to no greater than 5.5% by weight.

11. The composition of claim 3, wherein the emollient consists of one or more emollients selected from the group of emollients consisting of: Dimethicone Octyl Palmitate, Isopropyl Myristate, and Sorbitan Laurate.

12. The composition of claim 3, wherein the solvent consists of water.

13. The composition of claim 3, wherein the solvent is water.

14. The composition of claim 10, wherein the solvent is water.

15. The method of claim 4, wherein the alcohol content of the composition is limited to no greater than 5.5% by weight.

16. The method of claim 4, wherein the solvent is water.

17. The method of claim 4, further comprising adding a biostatic anti-microbial.

18. The method of claim 4, wherein the antioxidant comprises an antioxidant selected from the group of antioxidants consisting of Vitamin E Tocopherol and Vitamin A Palmitate.

* * * * *